US006885762B2

(12) United States Patent
Saha et al.

(10) Patent No.: US 6,885,762 B2
(45) Date of Patent: Apr. 26, 2005

(54) SCALE-BASED IMAGE FILTERING OF MAGNETIC RESONANCE DATA

(75) Inventors: Punam Kumar Saha, Philadelphia, PA (US); Jayaram K. Udupa, Audobon, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 518 days.

(21) Appl. No.: 09/779,032

(22) Filed: Feb. 7, 2001

(65) Prior Publication Data

US 2002/0035323 A1 Mar. 21, 2002

Related U.S. Application Data

(60) Provisional application No. 60/181,688, filed on Feb. 7, 2000.

(51) Int. Cl.$^7$ ................................................ G06K 9/00
(52) U.S. Cl. ...................... 382/131; 382/264; 324/310; 378/23
(58) Field of Search ................................ 328/128, 129, 328/130, 131, 132, 133, 134, 154, 168, 181, 193, 194, 203, 210, 221, 232, 237, 254, 255, 260, 264, 270, 274, 285, 307; 324/300, 301, 307, 318, 319, 320, 310; 378/23, 50, 98.6; 250/453.11, 482.1; 377/10; 356/39, 340; 345/424, 531; 702/150; 600/408; 424/9.6; 382/260

(56) References Cited

U.S. PATENT DOCUMENTS

| | | | | |
|---|---|---|---|---|
| 5,528,365 A | * | 6/1996 | Gonatas | 356/340 |
| 5,560,360 A | * | 10/1996 | Filler et al. | 600/408 |
| 5,644,646 A | * | 7/1997 | Du et al. | 382/128 |
| 5,743,266 A | * | 4/1998 | Levene et al. | 600/458 |
| 5,969,524 A | * | 10/1999 | Pierpaoli et al. | 324/307 |
| 5,991,701 A | * | 11/1999 | Triano | 702/150 |
| 6,159,445 A | * | 12/2000 | Klaveness et al. | 424/9.6 |
| 6,249,121 B1 | * | 6/2001 | Boskamp et al. | 324/318 |
| 6,556,720 B1 | * | 4/2003 | Avinash | 382/260 |

OTHER PUBLICATIONS

Gerig G, O Kilbler, R Kikinis, FA jolesz, "Nonlinear Anisotropic Filtering Of MRI Data," IEEE Transactions on Medical Imaging, 11(2):221–232 (1992).*

Ahn CB, YC Song, DJ Park, "Adaptive Template For Signal To Noise Ratio Enhancement In Magnetic Resonance Imaging," IEEE Transactions on Medical Imaging 18(6):549–556 (1999).

Bajla I, M Srámek "Improvement Of 3D Visualization Of The Brain Using Anisotropic Diffusion Smoothing Of MR Data," Proc. MEDINFO Part 1:683–686 (1995).

Chan P, JL Lim, "One Dimensional Processing For Adaptive Image Restoration," IEEE Transactions on Acoustic, Speech, and Signal Processing 33(1): 117–126 (1985).

(Continued)

Primary Examiner—Bhavesh M. Mehta
Assistant Examiner—Seyed Azarian
(74) Attorney, Agent, or Firm—Evelyn H. McConathy; Drinker Biddle & Reath LLP

(57) ABSTRACT

The invention provides novel scale-based filtering methods that use local structure size or "object scale" information to arrest smoothing around fine structures and across even low-gradient boundaries. One method teaches a weighted average over a scale-dependent neighborhood; while another employs scale-dependent diffusion conductance to perform filtering. Both methods adaptively modify the degree of filtering at any image location depending on local object scale. This permits a restricted homogeneity parameter to be accurately used for filtering in regions with fine details and in the vicinity of boundaries, while at the same time, a generous filtering parameter is used in the interiors of homogeneous regions.

20 Claims, 7 Drawing Sheets

(a)

(b)

OTHER PUBLICATIONS

Falcão AX, JK Udupa, S Samarasekera, S Sharma, "User–Steered Image Segmentation Paradigms: Live Wire and Live Lane," *Graphical Models Image Processing* 60:233–260 (1998).

Gerig G, O Kilbler, R Kikinis, Fa Jolesz, "Nonlinear Anisotropic Filtering Of MRI Data," *IEEE Transactions on Medical Imaging*, 11(2):221–232 (1992).

Jackson EF, PA Narayanan, JS Wolinskiy, TJ Doyle, "Accuracy And Reproducibility In Volumetric Analysis Of Multiple Sclerosis Lesions," *J. Computer Assisted Tomography* 17(2):200–205 (1993).

Kaufmann A, *Introduction To The Theory Of Fuzzy Subsets* 1:1–7, Academic Press (1975).

Lee JS "Digital Image Enhancement And Noise Filtering By Use Of Local Statistics," *IEEE Transactions On Acoustic, Speech, And Signal Processing*, vol. 2(2), 165–168 (1980).

Lifshitz LM, SM Pizer, "A Multiresolution Hierarchical Approach To Image Segmentation Based On Image Extrema," *IEEE Transactions On Pattern Analysis And Machine Intelligence* 12(6):529–540 (1990).

Lindeberg T, *Scale–Space Theory In Computer Vision*, Pp. 1–21(1994).

Maintz J, P Van Den Elsen, M Viergever, "Comparison Of Edge–Based And Ridge–Based Registration Of CT and MR Brain Images," *Medical Image Analysis* 1: 1–35–51 (1996).

Mcauliffe MJ, D Eberly, DS Fritsch, EL Chaney, SM Pizer, "Scale–Space Boundary Evolution Initialized By Cores," *Proc. Visual. In Biomed. Computing, Lecture Notes In Computer Science* 1131:173–182 (1996).

Parker GJM, JA Schnabel, "Enhancement Of Anisotropic Diffusive Filtering Of MR Images Using Approximate Entropy," *Proc. Intl. Soc. Of Magnet Resonance In Medicine* 7:175 (1999).

Perona P, J Malik, "Scale–Space And Edge Detection Using Anisotropic Diffusion," *IEEE Transactions On Pattern Analysis And Machine Analysis* 12(7):629–639 (1990).

Pizer SM, D Eberly, DS Fritsch, BS Morse, "Zoom–Invariant Vision Of Figural Shape: The Mathematics Of Cores," *Computer Vision And Image Understanding* 69(1):55–71 (1998).

Rank K, R Unbehauen, "An Adaptive Recursive 2D Filter For Removal Of Gaussian Noise In Images," *IEEE Transactions On Image Processing* 1(3):431–436 (1992).

Rosenfeld A, Ac Kak, *Digital Picture Processing*, Academic Press 1:236–267 (1982).

Rosner B, *Fundamentals Of Biostatistics*, Duxbury Press (1995).

Saha PK, JK Udupa, "Scale–Based Filtering Of Medical Images," *Medical Imaging 2000: Image Processing* In *Proceedings Of SPIE* 3979:735–746 (2000).

Saha PK, JK Udupa, D Odhner, "Scale–Based Fuzzy Connected Image Segmentation: Theory, Algorithms, And Validation," *Computer Vision And Image Understanding* 77:145–174 (2000).

Sahoo PK, S Soltani, AKC Wong,YC Chen, "A Survey Of Thresholding Techniques," *Computer Vision Graphics And Image Processing* 41:223–260 (1988).

Udupa JK, "Three–Dimensional Visualization And Analysis Methodologies: A Current Perspective," *Radiographics* 19:783–806 (1999).

Udupa JK, S Samarasekera, "Fuzzy Connectedness And Object Definition: Theory, Algorithms, And Applications In Image Segmentation," *Graphical Models And Image Processing* 53(3):246–261 (1996).

Wang DCC, AH Vagucci, CC LI, "Gradient Inverse Weighted Scheme And The Evaluation Of Its Performance," *Computer Graphics And Image Processing* 15:167–181 (1981).

Wang X, "On Gradient Inverse Weighted Filter," *IEEE Transactions On Signal Processing* 40(2):482–484 (1992).

Wells WM, P Viola, H Atsumi, S Nakajima, R Kikinis, "Multimodal Image Registration By Maximization Of Mutual Information," *Medical Image Analysis* 1:151–161 (1996).

\* cited by examiner (a) (b)

(a)

(b)

(c)

(d)

(e)

(f)

(a)

(b)

(c)

(d)

(e)

(a)

(b)

(c)

(d)

(e)

(f)

(a)

(b)

(c)

(d)

SCALE-BASED IMAGE FILTERING OF MAGNETIC RESONANCE DATA

REFERENCE TO RELATED APPLICATIONS

This application claims priority to U.S. Provisional Application No. 60/181,688 filed Feb. 7, 2000.

GOVERNMENT SUPPORT

This work was supported in part by a grants from the National Institutes of Health, grant number NS37172, and a grant from US Department of the Army, DAMD 179717271.

FIELD OF THE INVENTION

This invention relates generally to the field of magnetic resonance imaging (MRI), image display, image processing and image filtering to enhance structure and reduce noise.

BACKGROUND OF THE INVENTION

Magnetic Resonance Imaging (MRI) has revolutionized radiological imaging of the internal structures of the human body. It has the advantage of being noninvasive and offers no known health hazards. A variety of MRI protocols are currently available, however image acquisition techniques often suffer from low signal-to-noise ratio (SNR) and/or contrast-to-noise ratio (CNR). Although many acquisition techniques are available to minimize these, post acquisition filtering is a major off-line image processing technique commonly used to improve the SNR and CNR. A major drawback of filtering is that it often diffuses/blurs important structures along with noise.

Two- and higher-dimensional images are currently available through sensing devices that operate on a wide range of frequency in the electromagnetic spectrum—from ultrasound to visible light to X- and γ-rays (Chu et al., *Foundation of Medical Imaging*, John Wiley Sons, Inc., New York, N.Y., 1993). The usefulness of any of these modalities depends on the perceptability of certain features in the created images. Acquired images are often degraded by various types of artifacts resulting in a lowering of signal-to-noise ratio (SNR) and contrast-to-noise ratio (CNR). Despite high adaptivity and robustness of the human visual perceptual system, low SNR and CNR often degrade the information contained in the image and its utility. Further, image artifacts affect many image processing tasks such as segmentation (Sahoo et al., *Computer Vision Graphics and Image Processing* 41:233–260 (1988); Udupa et al., *Graphical Models and Image Processing* 58(3):246–261 (1996)), registration (Wells et al., *Medical Image Analysis* 1:35–51 (1996); J. Maintz et al., *Medical Image Analysis* 1:151–161 (1996)), and visual rendition (Udupa, *Radiographics* 19:783–806 (1999); Höhne et al., (eds.), *3D Imaging in Medicine: Algorithms, Systems, Applications*, Springer-Verlag, Berlin, 1990), which are crucial in many applications. Therefore, noise reduction, that is, the improvement of SNR and CNR, is of considerable interest in many imaging applications.

There are basically two approaches for improving SNR and CNR: by changing the method of image acquisition and by utilizing post-acquisition image processing. Improving the method of acquisition usually entails lengthening the acquisition time, or sacrificing spatial resolution, or upgrading of the imaging device hardware. Filtering is an off-line image processing approach, which, if properly designed, may be less expensive than, and as effective as, acquisition improvement approaches without having to sacrifice spatial resolution.

The aim of filtering is to enhance wanted (structure) information and to suppress unwanted (noise) information. Filtering operations may be classified into two categories—enhancing (also know as high pass filtering), wherein wanted information is enhanced hopefully without affecting unwanted information, and suppressing (also known as low-pass filtering), wherein unwanted information is suppressed hopefully without affecting wanted information.

Noise reducing filtering operations may be classified into two major categories. The first is space-invariant filtering (Rosenfeld and Kak, *Digital Picture Processing*, Academic Press, Inc., Orlando, Fla., 1982), wherein a spatially independent fixed smoothing operation is performed over the entire image. The other is space-variant filtering (Lee, *IEEE Transactions on Pattern Analysis and Machine Analysis* 2:165–168 (1980)), wherein the smoothing operation is modified by local image features.

A major drawback of space-invariant filtering techniques is that, along with noise, they often blur important structures. To overcome this problem, a variety of local image feature-dependent adaptive filtering strategies have been developed, including local image-statistics-driven filtering (Lee, 1980), least-squares error filtering (Chan and Lim, *IEEE Transactions on Acoustic, Speech, and Signal Processing* 33:117–126 (1985)), gradient inverse-weighted filtering (Wang et al., *Computer Graphics and Image Processing* 15:167–181 (1981); Wang, *IEEE Transactions on Signal Processing* 40:482–484 (1992)), multiple model Kalman filtering (Woods et al., *IEEE Transactions on Pattern Analysis and Machine Analysis* 9:245–253 (1987)), adaptive recursive filtering using local image features (Rank et al., *IEEE Transactions on Image Processing* 1:431–436 (1992)), local shape-based template-matched adaptive filtering (Ahn et al., *IEEE Transactions on Medical Imaging* 18:549–556 (1999)), and gradient-controlled anisotropic diffusive filtering (Perona et al., *IEEE Trans-actions on Pattern Analysis and Machine Analysis*, 12:629–639 (1990)). This later method has become quite popular, and has been further extended and utilized (Gerig et al., *IEEE Transactions on Medical Imaging* 11:221–232 (1992); Jackson et al., *J. Computer Assisted Tomography* 17:200–205 (1993); Bajla et al., *Proc. MEDINFO*, Part 1:683–686 (1995); Parker et al., *Proc. International Society of Magnetic Resonance in Medicine* 7:175(1999)) in a variety of applications.

Anisotropic diffusive filtering (Perona et al., 1990) provides a method, in which in each iteration, intensity diffusion takes place between every two spatially close image spatial elements ('spels'). The magnitude of the diffusion between the two spels is determined by the magnitude of the gradient of image intensity between them. It varies in a monotonically, non-decreasing manner up to a certain gradient magnitude value, and subsequently changes in a monotonically, non-increasing fashion. The flow across boundaries is thus significantly reduced by utilizing information about the presence of boundaries provided by intensity gradients.

A significant drawback of this very useful approach, however, is that it does not offer any image-dependent guidance for selecting the optimum gradient magnitude. More importantly, since it does not use any morphological or structural information to control the extent of diffusion in different regions, fine structures often disappear and fuzzy boundaries are further blurred upon filtering.

Thus, until the present invention, there has remained a need in the art for a reliable method for filtering SNR and CNR in an MRI acquired image in which intensity gradients are accurately determined, but in which selection of the optimum gradient magnitude is permitted and fine structures are detected. To overcome the problems of diffusive filtering in the prior art, the inventors have explicitly utilized 'object size' information—or 'scale'—to control the degree of smoothing that is done in different regions of the image. The notion of scale, as defined herein, is different from the term 'scale' used in scale-space computer vision literature (Lindeberg, *Scale-Space Theory in Computer Vision*, Boston, Mass.: Kluwer, 1994; Lifshitz et al., *IEEE Transactions on Pattern Analysis and Machine Intelligence* 12(6):529–5407 (1990); McAuliffe et al., in *Proc. Visualization in Biomedical Computing, Lecture Notes in Computer Science*, 1131, Springer Verlag, Berlin, 1996, pp. 173–182; Pizer et al., *Computer Vision and Image Understanding*, 69(1):55–71 (1998)), although the intent is the same, i.e., to tailor the processing to local object size.

SUMMARY OF THE INVENTION

The invention provides novel space-variant anisotropic (scale-based) methods for filtering SNR and CNR in an MRI acquired image—a spatial-resolution adaptive scale-computation method, and a scale-based neighborhood averaging method, and a scale-based diffusive filtering method—both of the scale-based methods outperform the anisotropic diffusive approach in the prior art. The present scale-based filtering methods use local structure size or "object scale" information to arrest smoothing around fine structures and across even low-gradient boundaries. One method uses a weighted average over a scale-dependent neighborhood, while another employs scale-dependent diffusion conductance to perform filtering.

Both methods adaptively modify the degree of filtering at any image location, depending on local object scale. This permits the accurate use of a restricted homogeneity parameter for filtering in regions with fine details and in the vicinity of boundaries, while at the same time, a generous filtering parameter is used in the interiors of homogeneous regions.

Scale-based filtering basically uses the local scale information at every spel to control the extent of filtering. By definition, the scale in regions with fine details or in the vicinity of boundaries is small. Thus, a restricted homogeneity parameter is used for filtering in small-scale regions (corresponding to fine structures and vicinity of boundaries), and to use a generous filtering parameter at large-scale regions (corresponding to interiors of large homogeneous regions).

Consequently, the local scale information indicates the radius of the largest hyperball of a "homogeneous" region centered at the spel. This concept was originally introduced by the inventors at the SPIE Conference Medical Imaging 2000, and further described in *Computer Vision and Image Understanding*, 77:145–174 (2000), where it was objectively demonstrated that the method significantly improve image segmentation based on fuzzy connectedness. Thus, the present invention provides a considerable body of evidence to show the effectiveness of the scale information in improving diffusive filtering, as well as for devising simple new strategies based on weighted averaging of intensities.

Qualitative comparison experiments based on both mathematical phantoms and medical (patient) MR images utilizing the anisotropic diffusion method and the two scale-based methods, showed significant improvements using the scale-based methods over the extant anisotropic diffusive filtering method in preserving fine details and sharpness of object boundaries. Quantitative analysis on geometric phantoms generated under a range of conditions of blurring, noise, and background variation confirmed the superiority of scale-based approaches embodied in the invention.

Thus, a scale-based filtering method of the invention is provided, wherein an enhanced MRI-acquired image is achieved for any selected MRI protocol, and for any selected region of a patient's body, by the steps comprising: imaging the region of the patient's body by the selected MR protocol to form an acquired image; and filtering the acquired image by a scale-based spatial resolution adaptive method using region-constancy based on local homogeneity to produce an enhanced image. The resulting image is enhanced in a manner independent of variations within or between patients, within or between tissues being imaged, or within or between MR devices used to acquire the image.

Also provided are computerized systems and devices for implementing the foregoing methods.

In addition, as provided in at least one embodiment, scale-based filtering methods of the invention are automated. Moreover, an embodiment of the invention is provided in which scale-based filtering methods are built into an MR scanner, permitting production of enhanced real time images.

Also provided is an enhanced MR image for imaging a region of the body of a patient according to one or more of the embodied scale-based filtering methods of the invention, including a scale-based neighborhood averaging method, or a scale-based diffusive filtering method. Further provided are apparatus or devices incorporating one or more of the foregoing features, including one or more of the embodied scale-based filtering methods of the invention to produce an MR image in which fine details and sharpness of object boundaries are preserved under a variety of conditions.

Additional objects, advantages and novel features of the invention will be set forth in part in the description, examples and figures which follow, and in part will become apparent to those skilled in the art on examination of the following, or may be learned by practice of the invention.

DESCRIPTION OF THE DRAWINGS

The foregoing summary, as well as the following detailed description of the invention, will be better understood when read in conjunction with the appended drawings. For the purpose of illustrating the invention, there are shown in the drawings, certain embodiment(s) which are presently preferred. It should be understood, however, that the invention is not limited to the precise arrangements and instrumentalities shown.

FIG. 1($a$) depicts a 2D slice from a MR 3D scene of the head of a multiple sclerosis patient. Using a suitable region-homogeneity parameter, a local determination is done to determine the largest disc that can be centered at any point, such as p, within which the intensities are homogeneous. The scale at p is bigger than that at q or at o. Scale is usually small in the vicinity of boundaries, such as at o. FIG. 1($b$) depicts the scale scene of the MR slice shown in FIG. 1($a$). In FIG. 1($b$), intensity at a location is proportional to the scale value at that location.

FIG. 2($a$) depicts an initial binary phantom scene. FIG. 2($b$) depicts a test phantom scene after blurring and adding a zero mean Gaussian noise and a slow varying (ramp) background component across columns. FIGS. 2(c) and 2(d) depict the scenes that resulted from filtering the scene in FIG. 2(b) by anisotropic diffusion for 3 and 10 iterations, respectively. FIGS. 2(e) and 2(f) depict the scenes that resulted from filtering the scene in FIG. 2(b) by scale-based diffusion for 3 and 10 iterations, respectively.

FIGS. 4(a) and 4(b) depict 2D scenes within two ROIs, one from the top left corner and the other from the bottom right corner of the original scene in FIG. 1(a). FIGS. 4(c)–4(h) depict filtered scenes (in 2D) corresponding to the scenes in FIGS. 4(a) and 4(b) that resulted from anisotropic diffusion (shown in FIGS. 4(c) and 4(d)), from scale-based neighborhood averaging (shown in FIGS. 4(e) and 4(f)), and from scale-based diffusion (shown in FIGS. 4(g) and 4(h)).

FIG. 5(a) depicts a 2D slice of the original 3D MR scene and the selected ROI. FIG. 5(b) depicts the scene within the ROI, magnified. FIGS. 5(c)–5(e) depict filtered scenes corresponding to the scene in FIG. 5(b) that resulted from 3D filtering using anisotropic diffusion (shown in FIG. 5(c)), using scale-based neighborhood averaging (shown in FIG. 5(d)), and using scale-based diffusion (shown in FIG. 5(e)).

FIG. 6(a) depicts an original phantom scene (one among 25 such scenes) at a low level of blurring and a medium level of noise, together with an intensity profile along the depicted bright horizontal line. Six ROIs are also shown within FIG. 6(a), which are used for FIG. 7. FIG. 6(b) depicts a magnified version of a section of the profile in FIG. 6(a), which section is shown at the bottom of FIG. 6(a) as a rectangle outlined in black. FIG. 6(c) depicts the profile corresponding to that in FIG. 6(b), but which were obtained for the original binary phantom scene after adding only the background ramp component (but not adding blurring and noise). FIG. 6(d)–6(f) depict profiles corresponding to that in FIG. 6(b), but which were obtained from the filtered scenes: by anisotropic diffusion (shown in FIG. 6(d)), by scale-based neighborhood averaging (shown in FIG. 6(e)), and by scale-based diffusion (shown in FIG. 6(f)).

FIG. 7(a) depicts scenes within the six ROIs taken from the unfiltered phantom scene. FIGS. 7(b)–7(d) depict the corresponding filtered scenes that resulted from anisotropic diffusion ((shown in FIG. 7(b)), from scale-based neighborhood averaging (shown in FIG. 7(c)), and from scale-based diffusion (shown in FIG. 7(d)).

DESCRIPTION OF PREFERRED EMBODIMENTS OF THE INVENTION

Figure 1:
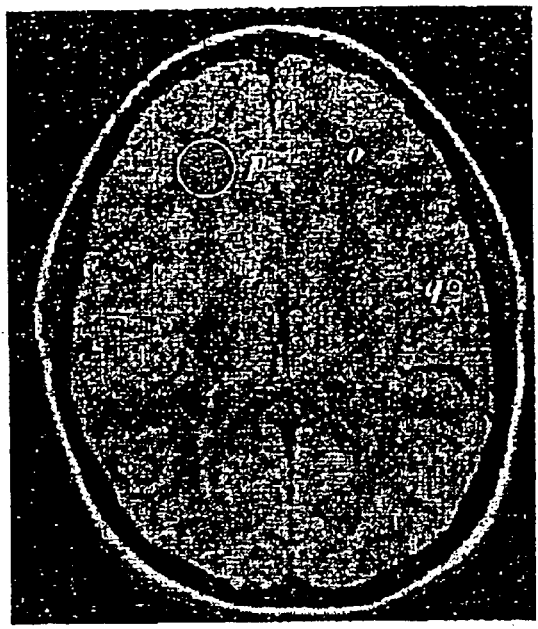
FIGS. 1($a$) and 1($b$) depict local structure size or scale.
Figure 1:
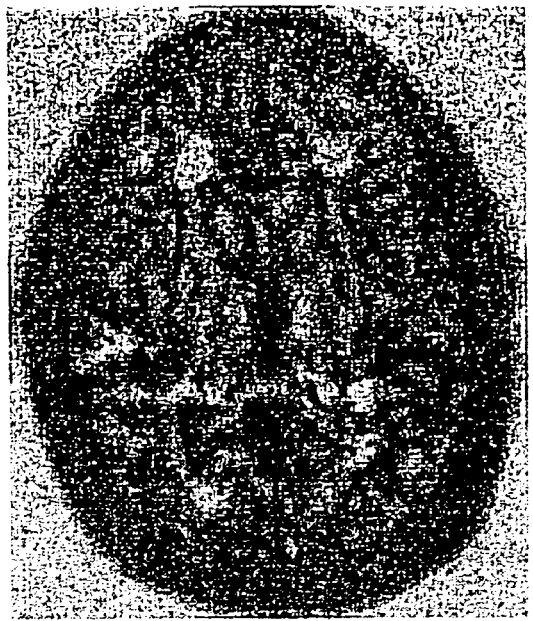

The invention provides novel scale-based MR image filtering methods, including scale-based neighborhood averaging and scale-based diffusion, which avoid or prevent blurring around fine structures and across boundaries using local structure size or "scale" information. Fundamentally, local structure size, or "scale", as defined by region homogeneity, improves the filtering operation by its utility in controlling the operation. The scale concept allows a restricted smoothing selectively to be achieved in the vicinity of boundaries and in fine structured regions, while at the same time allowing more generous filtering in the interiors. Thus, a scale-based filtering method of the invention is provided, wherein an enhanced MRI-acquired image is achieved for any selected MRI protocol, and for any selected region of a patient's body, by the steps comprising: imaging the region of the patient's body by the selected MR protocol to form an acquired image; and filtering the acquired image by a scale-based spatial resolution adaptive method using region-constancy based on local homogeneity to produce an enhanced image.

In the discussion which follows, both scale computation and the filtering operation are set up in a general n-dimensional framework, which also takes into account the anisotropy of spatial resolution. The framework is designed in such a way that there is only one parameter to be specified—the sole image-dependent homogeneity parameter—and methods are provided for selecting this parameter utilizing either user guidance or global image statistics. However, to better understand the present disclosure, certain terms and notations are defined as follows.

Most digital imaging systems produce images on a rectangular grid where the basic image elements, referred to as "spels," are hypercuboids. The term "spels" is an abbreviation for spatial elements; in 2D spels are 'pixels,' while in 3D they are 'voxels.' Mathematically, this is explained by letting n-dimensional Euclidean space $\Re^n$ be divided into hyper cuboids by n orthogonal families, each of equally distant parallel planes. Let v be an n-tuple whose $i^{th}$ element $v_i$ represents the distance between two successive parallel planes perpendicular to the $i^{th}$ coordinate axis. (A 'tuple' is a recognized term, simply referring to a mathematical relation between its attributes.) In other words, $v_i$ is the size of each spel along the direction of the $i^{th}$ coordinate axis.

The term v as used herein means the resolution of the grid system. Further, a coordinate system is chosen such that the centroid of each spel has the coordinates of the form ($c_1 v_1$, $c_2 v_2, \ldots, c_n v_n$) where $c_i$'s are integers. Thus, a one-to-one and onto mapping between the set of spels and $Z^n$ as follows: an n-tuple c, denoting a point in $Z^n$, is mapped to a spel, such that $c_j v_j$, for $1 \leq j \leq n$, gives the $j^{th}$ coordinate of the center of the spel represented by c. With this interpretation of spels, $Z^n$ itself represents the set of all spels of $\Re^n$, and concepts of spels and points denoting their centroids may, therefore, be used interchangeably to describe the invention.

For computational simplicity, a hard relation of adjacency was used for α in all experiments; however, fuzzy relations for α should also be considered, especially those functional forms for $\mu_\alpha$, which closely resemble the point-spread function of the imaging device. A fuzzy relation α on $Z^n$ is said to be a "fuzzy spel adjacency" if it is reflexive and symmetric (for a description of 'fuzzy relations,' see Kaufmann, *Introduction to the Theory of Fuzzy Subsets*, 1, Academic Press, New York, 1975). It is desirable that α be such that its membership value $\mu_\alpha(c, d)$, for any c, d∈$Z^n$, is a non-increasing function of the distance $\|c-d\|$ between c and d, where $\|\cdot\|$ denotes any L2 norm in $\Re^n$.

The functional form of $\mu_\alpha$ that is used for the image processing results presented herein, is as follows (however, a general functional form for $\mu_\alpha$ is considered for all formulations). For any spel c, $\mu_\alpha(c, c)=1$. Further, for any spels c and d, $\mu_\alpha(c, d)=1$, if c and d differ in exactly one coordinate by 1. Otherwise, $\mu_\alpha(c, d)=0$.

In 2D:

$$\mu_\alpha(c, d) = \begin{cases} 1, & \text{if } c = d \text{ or } c, d \text{ are 4-adjacent,} \\ 0, & \text{otherwise.} \end{cases} \quad \text{(Equation 1)}$$

Thus, it is readily seen that α is indeed a fuzzy spel adjacency. The triplet ($Z^n$, α, v) is, therefore, called a "fuzzy digital space," in which α is any fuzzy spel adjacency, and v is the resolution of the grid system. A fuzzy digital space is a concept that characterizes the underlying digital grid system, independently of any image-related notions.

A "scene over a fuzzy digital space" ($Z^n$, α, v) is a pair C=(C, f), where C={c|$-b_j \leq c_j \leq b_j$ for some b∈$Z_+^n$}, $Z_+^n$ is the set of n-tuples of positive integers, f is a function domain is C, called the "scene domain", and whose range is a set of integers [L, H]. The terms "scene" and "image" are used interchangeably, herein, as recognized in the art. The invention generalizes in a straightforward manner to vector-valued scenes, i.e., when f is a vector-valued function. However, for the sake of simplicity of description, f is treated herein as a scalar-valued function. A scene Cover the triple ($Z^n$, α, v) is referred to as a "binary scene" if the range of f is {0, 1}.

1) Anisotropic Diffusive Filtering.

A diffusive filtering process can be defined using the divergence operator 'div' on a vector field. A mathematical formulation of the diffusion process on a vector field V at a point c in coordinate-free form is given by:

$$\frac{\partial f}{\partial t} = div\, V = \lim_{\Delta\tau \to 0} \int_S V \cdot ds, \quad \text{(Equation 3)}$$

wherein Δτ is the volume enclosed by the surface s (surrounding c), and ds=uds, wherein u is the unit-vector normal and outward-directed to the 'infinitesimal' surface element ds. The diffusion process is controlled by the intensity flow vector field V. The functional form for flow is defined as $$V=GF, \quad \text{(Equation 4)}$$

wherein G is the diffusion-conductance function, and F is the scene intensity gradient vector field.

In an isotropic diffusion, the conductance function G is constant, and it has been argued by Perona et al., 1990, that such diffusion methods blur object boundaries and structures. As a result, Perona et al, proposed an anisotropic diffusion method in which G is spatially varied as a non-linear function of the magnitude of the scene intensity gradient, such that the conductance function encourages smoothing within a region (characterized by low intensity gradients) in preference to smoothing across boundaries (characterized by high intensity gradients).

2) Scale-Based Filtering.

Although, the main motivation for anisotropic diffusive filtering was to reduce noise while minimizing blurring across boundaries, since it does not account for local structure size, it often loses/blurs fine structures and diffuses across boundaries. This phenomenon is illustrated in FIGS. 2, 4–7, which will be discussed in greater detail below.

In this section, however, two scale-based filtering methods are presented that use the structure size information to accurately arrest diffusion around fine structures, and across even low gradient boundaries. The size of local structures is determined at every spel under a pre-specified scene-dependent, region-homogeneity criterion, and then the generosity of filtering is controlled using this parameter. For example, in FIG. 1(a), which is a 2D slice from a MR 3D scene of the head of a multiple sclerosis patient, using a suitable region-homogeneity parameter, a local determination is done to determine the largest disc that can be centered at any point, such as p, within which the intensities are homogeneous. In FIG. 1(a), the size of the local structure to which pixel p belongs is bigger than that to which q or o belong. The scale is usually small in the vicinity of boundaries, such as at o. It is, therefore, reasonable to allow a more generous filtering at p (i.e., an averaging over a larger neighborhood, or a diffusion using a higher conductance), than that at q or at o.

The theory of defining scale as the size of the local structure and utilizing scale in carrying out local operations was originally proposed by the inventors (Saha et al, 2000, herein incorporated by reference). Following the same line of reasoning, "scale" in a scene C at any spel, c∈C, is defined as the radius, r(c), of the largest hyperball centered at c, which lies entirely in the same object region (defined under a pre-specified region-homogeneity criterion). Ironically, it appears that object definition is first needed to determine scale. Thus, a simple and effective algorithm (presented in the following section, as Algorithm OSE) has been defined by the inventors (see also Saha et al., 2000), which estimates r(c) at every spel, c∈C, in any scene C without explicit object segmentation, but based on continuity of region homogeneity. This 'rough' object size information is utilized to control the diffusion process so as to improve diffusive filtering and to devise a simple neighborhood averaging strategy that can also out-perform diffusive filtering.

2.1) Computation of Scale.

A "hyper ball $B_{k,v}(c)$ of radius k≥0 and with center at c∈C in a scene C=(C, f) over ($Z^n$ α, v) is defined by:

$$B_{k,v}(c) = \left\{ e \in C \;\middle|\; \sqrt{\sum_{i=1}^n \frac{v_i^2(c_i - e_i)^2}{\min_j [v_j^2]}} \leq k \right\}. \quad \text{(Equation 5)}$$

wherein the term e is defined within the equation as a spel belonging to C.

Note that $B_{k,v}(c)$ forms a digital hyper ball when the spatial resolution is isotropic, and a digital hyper ellipsoid when it is not. The equation is formulated so that, in both cases, $B_{k,v}(c)$ represents a (quantized) hyper ball in the scene domain. For the purposes of the invention, $B_{k,v}(c)$ is referred to as a hyper ball, irrespective of whether or not v is isotropic.

For a hyper ball $B_{k,v}(c)$ of any radius k>0, and centered at c, a fraction, $FO_{k,v}(c)$ ("fraction of object"), is defined to indicate the fraction of the ball boundary occupied by a region which is sufficiently homogeneous with c, by:

$$FO_{k,v}(c) = \frac{\sum_{e \in B_{k,v} - B_{k-1,y}(c)} W_\Psi(|f(c) - f(e)|)}{|B_{k,v}(c) - B_{k-1,v}(c)|}$$ (Equation 6)

wherein $|B_{k,v}(c) - B_{k-1,v}(c)|$ is the number of spels in (i.e., the volume of) $B_{k,v}(c) - B_{k-1,v}(c)$ and $W_\psi$ is a homogeneity function. A detailed description of the characteristics of $W_\psi$ is found in Saha et al., 2000, herein incorporated by reference. The membership functions utilized in fuzzy subset theory corresponding to the fuzzy proposition "x is small" can be used for $W_\psi$. A zero-mean, unnormalized, Gaussian function is a preferred choice for $W_\psi$.

The algorithm for object scale estimation is presented below as Algorithm OSE, wherein "OSE" refers to "Object Scale Estimation." It has been modified from that which was originally presented by Saha et al., 2000, to account for resolution anisotropy of acquired scenes.

---

Algorithm OSE
Input: C, c ∈ C, $W_\psi$, a fixed threshold $t_s$.
Output: r(c).
begin
    set k = 1;
    while $FO_{k,v}(c) \geq t_s$ do
        set k to k + 1;
    endwhile;
    set r(c) to k − 1;
output r(c);
end.

---

The algorithm iteratively increases the ball radius k by 1, starting from 1, and checks for $FO_{k,v}(c)$, the fraction of the object containing c that is contained in the ball. The first time that this fraction falls below $t_s$, the ball then contains an object region different from that to which c belongs.

In accordance with Saha et al., 2000, $t_s$=0.85 is used. The rationale for this choice is as follows: In a 3×3 neighborhood of a pixel c, in a 2D scene, C, one out of the eight neighboring pixels may belong to a different object (to account for noise), but the neighborhood is still considered to be entirely within the same object. This leads to $t_s$=7/8. No significant change in the results was observed by varying $t_s$ in the range $0.8 \leq t_s \leq 0.9$.

To complete the description of scale computation, the following is a description of two methods by which a proper value is selected for region-homogeneity parameter $\sigma_\psi$. In the first, which is an operator interactive training-based method, an operator using a mouse controlled brush, paints on a display of a slice of an image to specify objects of interest, excluding inter-object boundaries. The mean, $M_h$, and the standard deviation, $\sigma_h$, of local intensity gradient magnitudes, are computed as the mean and the standard deviation of the intensity differences, $|f(c)-f(d)|$, for all possible pairs (c, d) of spels in the painted regions, such that c≠d and $\mu_\alpha(c,d)>0$. These estimates are then used to set up the value of the homogeneity parameter as follows:

$$\sigma_\psi = M_h + t_h \sigma_h,$$ (Equation 7)

wherein $t_h$ is a constant, and its value is set to 3. This is based on the rationale that in a normal distribution, 3 standard deviations on the two sides of the mean cover 99.7% of the population.

The second method of selecting $\sigma_\psi$ is similar to the preceding method, except that it requires no operator intervention. Instead of computing the mean and the standard deviation of local intensity gradients over the painted regions, the local, in-plane intensity gradients (i.e., c and d are in the same plane) are first determined over the entire scene domain. Local, out-of-plane intensity gradients are excluded because, in most medical imaging applications, the out-of-plane resolution is relatively coarse. However, local out-of-plane intensity gradients may be used when the spatial resolution is isotropic. The upper 10th percentile of the gradients are then discarded in order to account for inter-object boundaries. The mean and the standard deviation are computed over the lower 90 percentile of the gradients. Finally, the expression in Equation 7 is used for determining $\sigma_\psi$. In this fashion, the only parameter required in the method is determined automatically.

In the examples that follow, the second method was used for computing $\sigma_\psi$. For example, the scale image shown in FIG. 1(b) corresponds to the MRI slice of the head of the patient shown in FIG. 1(a). In the scene in FIG. 1(b), intensity at a location is proportional to the scale value at that location. As can be seen, the interior regions have higher scale (brighter intensities), while in contrast, the detailed structural regions, as well as the regions in the vicinity of boundaries, have lower scale (darker intensities).

2.2) Scale-based Neighborhood Averaging.

A fixed (Gaussian) kernel-based filtering method essentially convolves the original scene with a fixed kernel. A major drawback of such a method is that, when the kernel is defined over a small neighborhood, the method fails to significantly increase the SNR upon filtering. On the other hand, when the kernel is defined over a large neighborhood, smaller shapes are lost and substantial amount of blurring takes place across boundaries. Finding an optimum neighborhood size (kernel) had been a fundamental problem in this type of approach in the prior art. By bringing object scale into the framework, not only is the size of the neighborhood specified, but also it is allowed to vary over the scene domain in a meaningful way. This allows large neighborhoods to be used in the interiors of large structures (e.g., at p in FIG. 1(a)), while small neighborhoods are used in fine, detailed regions and in the vicinity of boundaries (e.g., at q or at o) in the same figure.

A scale-based neighborhood averaging method can be formally defined as creating an output filtered scene $C_{sa}$=(C, $f_{sa}$) for an input scene C=(C, f) over ($Z_n$, α, v), where, for any c∈C, $$f_{sa}(c) = \frac{\sum_{e \in B_{r(c),v(c)}} f(e) \omega_c \left( \sqrt{\sum_{i=1}^{n} \frac{v_i^2(c_i - e_i)^2}{\min_j [v_j^2]}} \right)}{\sum_{e \in B_{r(c),v(c)}} \omega_c \left( \sqrt{\sum_{i=1}^{n} \frac{v_i^2(c_i - e_i)^2}{\min_j [v_j^2]}} \right)}$$ (Equation 8)

wherein $\omega_c$ is a distance-dependent weighting function. The true distance between c and e is used for the weighting function $\omega_c$, with the purpose being to develop a scale-dependent filtering kernel using $B_{r(c), v}(c)$. The filtering kernel $\omega_c$ should satisfy the following properties:

1. The domain of $\omega_c$ is the set of non-negative numbers.
2. The range of $\omega_c$ is [0,1] and $\omega_c(0)=1$.
3. There is one control parameter $\sigma_{\omega_c}$ of $\omega_c$, such that for a given distance between c and e, $\omega_c$ is monotonically non decreasing with $\sigma_{\omega_c}$.
4. For any given control parameter $\sigma_{\omega_c}$, $\omega_c$ is monotonically non-increasing with the distance between c and e.

In the fuzzy subset theory, the membership functions corresponding to the fuzzy proposition "x is small" satisfy these properties. Three such popular functions are (1) unnormalized Gaussian, (2) ramp, and (3) box window. In the examples that follow, an unnormalized Gaussian function for $\omega_c$ was used. Intuitively, it follows that $\sigma_{\omega_c}$ should be a function of r(c), and accordingly $\sigma_{\omega_c}$=r(c) is used.

2.3) Scale-based Diffusive Filtering.

In the original anisotropic diffusion method, flow across objects is reduced due to high intensity gradients at boundaries. Intensity gradients at spels on blurred boundaries, where gradient is distributed over a thick boundary band, are often not high enough to arrest flow. As a result, diffusion flow takes place across blurred boundaries. The effect of this phenomenon becomes visually prominent when the filtering method is executed for several iterations. Within an 'iteration,' estimated intensity flow diffuses between every two adjacent spel in the image domain. This effect is demonstrated in FIG. 2(d), wherein the diffusion process is run for 10 iterations on the 2D scene shown in FIG. 2(b).

Thin and fine structures in images often fade or disappear, even after fewer than 10 iterations of anisotropic diffusion. The behavior of anisotropic diffusion around thin and fine structured regions is further discussed in the Examples that follow; see also FIGS. 4, 5 and 7.

The purpose behind scale-based diffusion is to effect a restricted diffusion around thin and fine structured regions and in the vicinity of boundaries, while at the same time allowing a generous diffusion in the interiors of homogeneous regions. This is achieved in the present embodiments by using a variable diffusion conductance function that is controlled by the scale parameter. As demonstrated in the section entitled Scale Based Filtering and shown in FIG. 1, scales in the vicinity of boundaries and in thin and fine structured regions are small, while with the interiors they are large, thus showing the effectiveness of a scale-dependent diffusion process. Compare FIGS. 2(c) with 2(e), which were obtained after 3 iterations, and FIG. 2(d) with 2(f), which were obtained after 10 iterations. See also FIGS. 4, 5, and 7.

However, before further describing the scale-based method, a discussion of the characteristics of diffusion conductance functions is needed.

Figure 3:
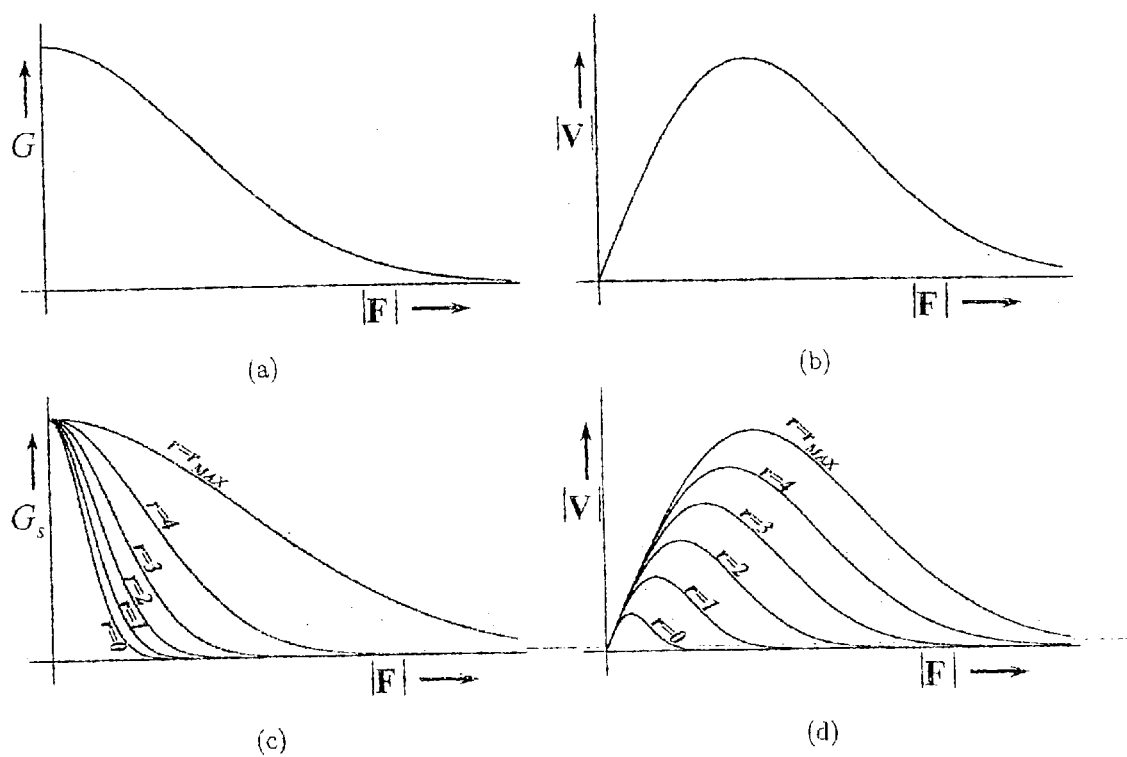
FIG. 3(a) graphically depicts the shape of diffusion conductance function that complies with the principle of nonlinear diffusion.
FIG. 3(b) graphically depicts the shape of diffusion flow magnitude function that complies with the principle of nonlinear diffusion.
FIG. 3(c) graphically depicts the shape of different conductance functions at different scales. The right-most curve of FIG. 3(c) represents the conductance function at maximum scale $r_{MAX}$.
FIG. 3(d) graphically depicts the shape of different diffusion flow magnitude functions at different scales. The right-most curve of FIG. 3(d) represents the diffusion flow magnitude at maximum scale $r_{MAX}$.

Perona et al, 1990, described qualitatively the shapes of the diffusion conductance function, G, and diffusion flow magnitude function, |V| (FIGS. 4 and 6 in Perona et al, 1990) that comply with the idea behind nonlinear diffusion. The required shapes of diffusion conductance and flow magnitude functions are shown in FIGS. 3(a) and (b), respectively. The necessary properties of G may be formulated as follows:

1. The domain of G is the set of all non-negative numbers.
2. The range of G is [0, 1], and G=1 when |F|=0, while G→0 when |F|→∞.
3. There is a control parameter $\sigma$, such that for any given |F| and $\sigma_1 < \sigma_2$, $G_{\sigma_1} \leq G_{\sigma_2}$.

Further, |V| (see Equation 4) has a maximum value at |F|=$\sigma$, and |V| is monotonically increasing for |F|<$\sigma$, while it is monotonically decreasing for |F|>$\sigma$.

Intuitively, it appears that G should be monotonically decreasing with |F|. However, not every monotonically decreasing function results in a valid flow function. For example, if G is selected in the expression $$G = \frac{1}{1 + \sqrt{|F|}},$$

the resulting conductance function is monotonically decreasing, but it does not result in a valid flow function because the latter is a throughout-increasing function of |F|, and it possesses no finite optimum. Therefore, care must be taken in selecting a conductance function so that the resulting flow function possesses a unique maximum. Two valid conductance functions were proposed in Perona et al, 1990, and Gerig et al., 1992.

$$G_1(F) = \frac{1}{1 + \left(\frac{|F|}{\sigma}\right)^{1+\beta}} \bigg| \beta > 0, \qquad \text{(Equation 9)}$$

and $$G_2(F) = e^{-\frac{|F|^2}{2\sigma^2}}. \qquad \text{(Equation 10)}$$

Both functional forms in both anisotropic and scale-based diffusion methods have been applied to patient MR images, and no significant visual differences were produced in the results. Consequently, the unnormalized Gaussian function of Equation 10 was used herein for all evaluations.

As described above, $\sigma$ is the control parameter that determines the generosity of filtering. When $\sigma$ is large, the generosity of filtering is high, and the possibilities of blurring across boundaries increase. On the other hand, when $\sigma$ is small, the generosity of filtering is low, and more noise survives after filtering. Following this principle, $\sigma$ may also be thought of as a region-homogeneity parameter.

As previously pointed out, the basic premise behind scale-based diffusion is to allow only a restricted diffusion at small-scale regions, while at the same time being generous at high-scale regions. This is achieved by using an adaptive homogeneity parameter $\sigma_s$, in place of $\sigma$ in Equation 10, as a monotonically, non-decreasing function of local scale. Consequently, $\sigma_s$ was used herein as a linear function of scale.

Given this understanding of scale-based diffusion conductance, the process of scale-based diffusion is completely described by Equations 3, 4, and 10. Accordingly, throughout the remainder of the disclosure, the details of the scale-based diffusion process are presented as applicable to a scene over ($Z_n$, $\alpha$, v). Like anisotropic diffusion, scale-based diffusion is also an iterative process, and let t denote the iteration number. Let C=(C, $f$) be the given scene, and let $C_t$=(C, $f_t$) denote the scene resulting from the diffusion process at the $t^{th}$ iteration. For any c, d∈C, such that c≠d and $\mu_\alpha$(c, d)≠0, let D(c, d) denote the unit vector along the direction from the point c toward the point d. Let $F_t$(c, d) represent the intensity gradient vector along D(c, d) given by $$F_t(c, d) = \frac{f_t(c) - f_t(d)}{\sqrt{\sum_{i=1}^{n} \frac{v_i^2 (c_i - e_i)^2}{\min_j [v_j^2]}}} D(c, d) \qquad \text{(Equation 11)}$$

Note that the preceding expression takes into account resolution anisotropy.

While determining the intensity flow from spel d to spel c, the effective scale, $r_{\text{eff}}(c, d)$, defined as follows, was utilized.

$$r_{\text{eff}}(c,d) = \min [r(c), r(d), r(e)] \quad \text{(Equation 12)}$$

wherein e∈C is the neighboring spel of c, just opposite to d, defined by e=c−(d−c). When c is in the border of the scene domain, e was let equal to c. Using this definition of effective scale, the diffusion conductance function, $G_t(c, d)$ for the flow from d to c at the $t^{th}$ iteration, is defined by:

$$G_t(c, d) = e^{-\frac{|F_t(c,d)|^2}{2[\sigma_s(c,d)]^2}} \quad \text{(Equation 13)}$$

wherein $\sigma_s(c, d)$ is the scale-adaptive region-homogeneity parameter used for controlling the intensity flow from d to c, given by $$\sigma_s(c, d) = \frac{\sigma_\psi \{1 + r_{\text{eff}}(c, d)\}}{1 + r_{\text{MAX}}}. \quad \text{(Equation 14)}$$

In this case $r_{MAX}$ is an upper limit on the scale in C, and in the following examples $r_{MAX}$=5. $\sigma_\psi$ is the homogeneity parameter defined above in Section 2.1, entitled Computation of Scale.

Accordingly, intensity flow vector $V_t(c, d)$ from spel c to spel d at the $t^{th}$ iteration is defined by:

$$V_t(c,d) = F_t(c,d)G_t(c, d) \quad \text{(Equation 15)}$$

Note that $V_t(c, d) \cdot D(c, d)$ is positive when $f_t(c) > f_t(d)$; it is negative otherwise; and it is zero when c=d or $f_t(c)=f_t(d)$. Thus, the flow direction between two spels is always such that it tries to reduce the gradient between them. FIG. 3(c) shows diffusion conductance functions at different scales while FIG. 3(d) shows the magnitude of intensity flow vector at different scales. As shown in the two figures, at the maximum scale $r_{MAX}$, conductance is highest and the flow magnitude is maximum. Moreover, both diffusion conductance and flow magnitude decrease as scale decreases.

With these formulations, the scale-based iterative process is defined by:

$$f_t(c) = \quad \text{(Equation 16)}$$
$$\begin{cases} f(c), & \text{for } t = 0, \\ f_{t-1} - K_D \sum_{d \in C} \mu_\alpha(c, d) V_{t-1}(c-d) \cdot D(c, d), & t > 0, \end{cases}$$

where $K_D$ is a constant. It can be shown in a manner analogous to the proof in Gerig et al., 1992, that in order to guarantee a "monotonic variation of spel intensities" (i.e., the intensity of any spel c∈C is either non-increasing or non-decreasing with iteration t, but is not oscillatory), the 'upper limit' of $K_D$ should satisfy the following inequality. For any C∈$Z^n$, $$K_D \leq \frac{1}{\sum_{d \in Z^n} \mu_\alpha(c, d)}. \quad \text{(Equation 17)}$$

Although $K_D$ has no lower limit, more iterations are needed to achieve the same degree of filtering when a small value for is used for $K_D$. In the following examples, the value $K_D$ was used at its upper limit. Thus, according to the adjacency criterion (see Equations 1 and 2), $K_D$=⅕ in 2D and $K_D$=⅐ in 3D.

The embodied methods of the invention are useful when implemented by recognized techniques to produce an automated, scale-based filtered image, and are particularly useful when installed by recognized methods in the art into an MR scanner, permitting production of enhanced real time images.

Also provided in the invention is an enhanced MR image for imaging a region of the body of a patient according to one or more of the embodied scale-based filtering methods of the invention, including a scale-based neighborhood averaging method, or a scale-based diffusive filtering method. Further provided in the invention are computerized apparatus and devices incorporating one or more of the embodiments of the invention, including one or more of the embodied scale-based filtering methods of the invention to produce an MR image in which fine details and sharpness of object boundaries are preserved under a variety of conditions.

EXAMPLES

The present invention is further described in the following examples in which both qualitative and quantitative experiments were conducted to assess the relative performance among the three methods—(1) anisotropic diffusion, (2) scale-based neighborhood averaging, and (3) scale-based diffusion. These examples are provided for purposes of illustration to those skilled in the art, and are not intended to be limiting unless otherwise specified. Moreover, these examples are not to be construed as limiting the scope of the appended claims. Thus, the invention should in no way be construed as being limited to the following examples, but rather, should be construed to encompass any and all variations which become evident as a result of the teaching provided herein.

The principles and algorithms for both scale-based neighborhood averaging and scale-based diffusion were as described above. Also as described, were how to determine the sole image-dependent parameter, $\sigma_\psi$, and how to fix other image-independent terms. For the anisotropic diffusion method, essentially the method of Gerig et al., 1992 was followed, except that in computing the image gradients, resolution anisotropy was considered as in Equation 11.

All experimental results presented in this paper were obtained using the functional form for diffusion conductance of scale-based neighborhood averaging in Gerig et al., 1992, which was the same as Equation 10, above. Since the Gerig et al. method did not describe selection of parameter κ, the following was used: $\kappa = \sqrt{2}\sigma = \sqrt{2}\sigma_\psi$ in Equation 10—the same parameter that was used for scale-based diffusion. Except for the result in FIG. 2(d), all results for anisotropic diffusion were obtained by applying the method for 3 iterations as recommended in Gerig et al., 1992, which is herein incorporated by reference. Except for the result in FIG. 2(f), all results for scale-based diffusion were obtained by applying the method for 7 iterations.

In Example 1, the three methods are qualitatively compared using a phantom image and MR images of the heads of multiple sclerosis patients. A quantitative comparison based on a phantom containing different geometric shapes is presented in Example 2, to more objectively assess the relative performance of each of the three methods.

Example 1

Qualitative Comparisons.

In this example, two case studies are presented from MR patient studies, and then two phantom experiments are described.

Comparative Case Study 1.1.

Figure 4:
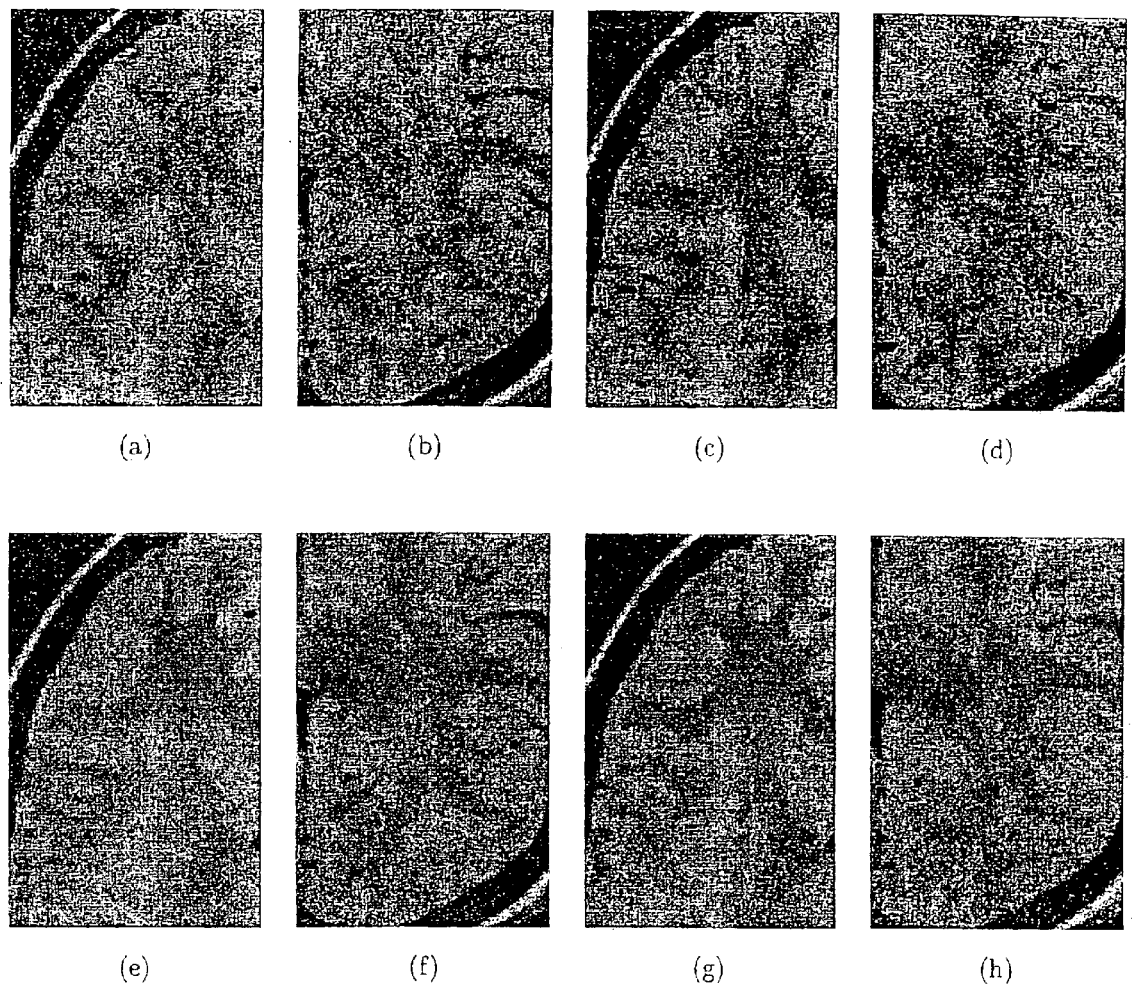
FIGS. 4(a)–4(h) depict comparisons among the three filtering methods using the 2D slice of a MR 3D scene of the head of a multiple sclerosis patient originally shown in FIG. 1(a).

In FIG. 4, the filtered output from the three methods is illustrated for two regions of interest (ROI)—one from the top-left corner and the other from the bottom-right corner—selected from the MR slice displayed in FIG. 1(a). The two ROIs, and the results from the three filtering methods, are shown in FIGS. 4(a)–4(h). FIGS. 4(c)–4(h) depict filtered scenes (in 2D) corresponding to the scenes in FIGS. 4(a) and 4(b) resulting from anisotropic diffusion (shown in FIGS. 4(c) and 4(d)), from scale-based neighborhood averaging (shown in FIGS. 4(e) and 4(f)), and from scale-based diffusion (shown in FIGS. 4(g) and 4(h)). As can be seen from all six filtered images (FIGS. 4(c)–4(h)), the smoothness in homogeneous regions seems visually to be the same in all images, while boundary contrast seems to be higher using scale-based methods, as opposed to using anisotropic diffusion. Also, scale-based methods were seen to preserve fine details (for example, the linear bright structure in the left, middle part of FIG. 4(b)) better than anisotropic diffusion. Moreover, among the two scale-based methods, differences did not appear to be visually significant.

Comparitive Case Study 1.2.

Figure 5:
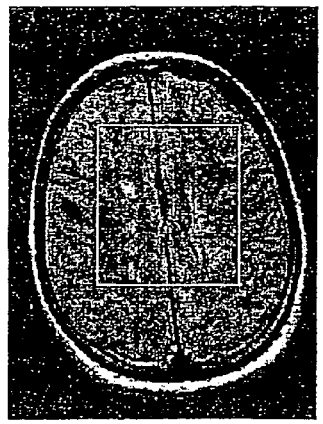
FIGS. 5(a)–5(e) depict comparisons among the three filtering methods using a 3D MR scene of the head of a multiple sclerosis patient.
Figure 5:
Figure 5:
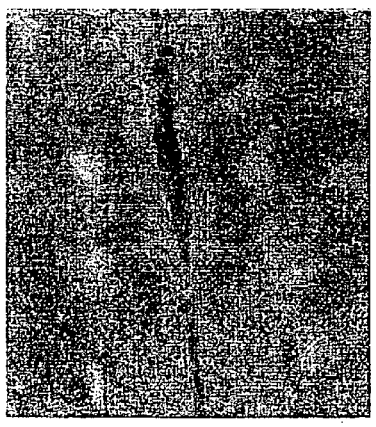
Figure 5:
Figure 5:
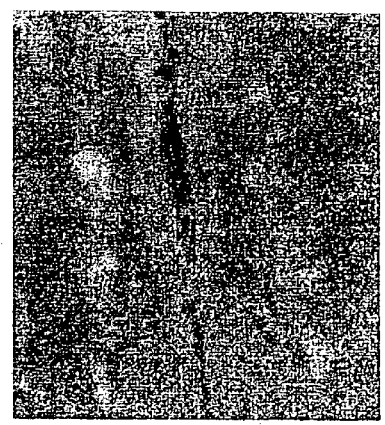

FIG. 5 illustrates 3D-comparative results among the three methods. All methods were applied on a proton density-weighted 3D MR scene of the head of a multiple sclerosis patient. The out-of-plane resolution was seen to be almost 3.5 times more coarse than the in-plane resolution. The results, thus, also demonstrate the behavior of the three methods under resolution anisotropy.

The size of the scene domain was 181×246×55, with a voxel size of 0.86×0.86×3.0 mm$^3$. In the non-optimized experimental implementation, the computation of scale took 10–12 seconds on a 450 MHz Pentium PC for the scene in FIG. 5, while each iteration of anisotropic and scale-based diffusion required 7–8 seconds. Compared to the anisotropic diffusion method, scale computation was clearly an extra step for the scale-based diffusion method. For the same scene, scale-based neighborhood averaging method took 17–18 seconds in total on the same machine, which is faster than anisotropic diffusion, which required 21–24 seconds when run for three (3) iterations. Moreover, the same improvement of SNR values was achieved in homogeneous regions whether anisotropic or scale-based diffusion was applied for the same number of iterations. However, more blurring was seen across boundaries and in fine structured regions in the anisotropic diffusion method.

Since it was not clear how to best display such 3D scenes (short of showing all slices at sufficiently high magnification), one slice is shown in FIG. 5(a) taken from the original scene with an ROI. A portion of the slice was zoomed up (magnified) in FIG. 5(b), to allow a closer scrutiny of the images. FIGS. 5(c)–(e) show the same ROI for the filtered scenes obtained using anisotropic diffusion (FIG. 5(c)), using scale-based neighborhood averaging (FIG. 5(d)), and using scale-based diffusion (FIG. 5(e)) methods, respectively. While there are no visually significant differences among the three methods in the level of smoothing within homogeneous regions, it can been seen that boundary contrast is significantly improved using the scale-based methods. Some of the lesions (hyper intense blobs) appear blurred in the filtered scene as a result of anisotropic diffusion, while by comparison, their contrast is retained using scale-based methods.

Although there is major resolution by anisotropy, the scale-based methods were able to retain boundary contrast and subtle structures. As between the two scale-based methods, the result using scale-based diffusion appears visually more pleasing than the result produced using scale-based neighborhood averaging.

Phantom Example 1.1.

Figure 2:
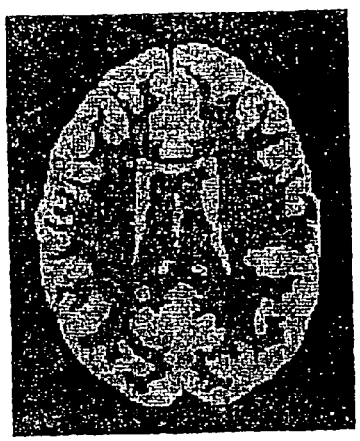
FIGS. 2($a$)–2($f$) depict diffusion flow across blurred object boundaries and the usefulness of object scale information to arrest such flows.
Figure 2:
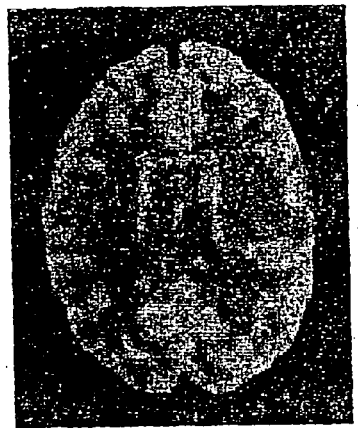
Figure 2:
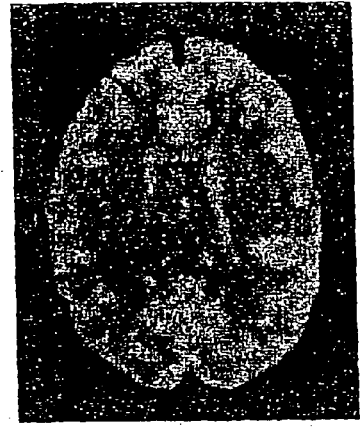
Figure 2:
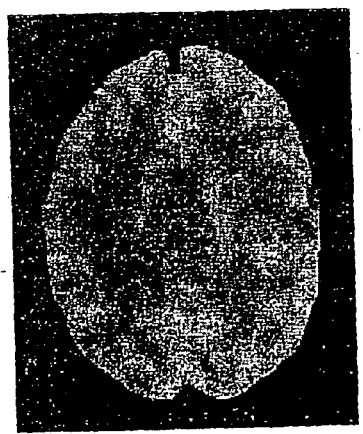
Figure 2:
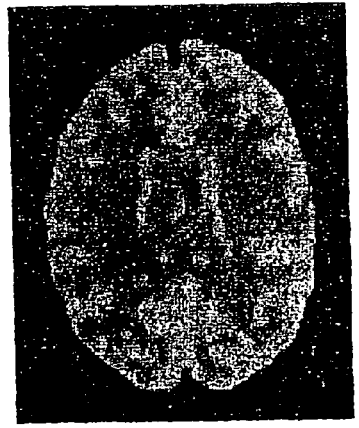
Figure 2:
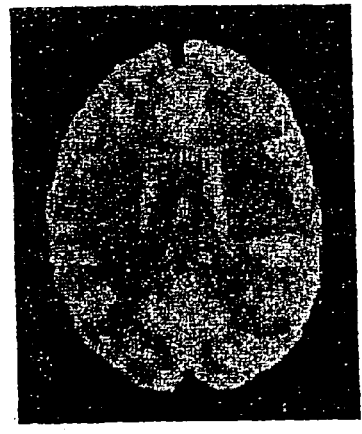

FIG. 2 demonstrates how diffusion proceeds across certain blurred object boundaries in the method of anisotropic diffusion (FIGS. 2(c) and 2(d)), whereas it is arrested in the scale-based method (FIGS. 2(e) and 2(f)). The 2D scene, shown in FIG. 2(b) was a test geometric phantom scene created after blurring and adding a zero mean Gaussian noise and a slow varying (ramp) background component across columns to imitate white matter and gray matter regions in the human brain. One slice was selected from a 3D proton density MR scene of the head of a multiple sclerosis patient undergoing routine clinical evaluation. Subsequently, the white matter and gray matter regions in the original scene were carefully segmented using a user-steered segmentation method (Falcão et al., *Graphical Models Image Processing* 60:233–260 (1998)). To the white matter region in the scene, a value was assigned equal to the average of the intensities within the white matter region in the original MR slice, and to the background region within the brain, a value was assigned equal to the average of the intensities within the gray matter region in the original MR slice.

From this starting scene, the 2D phantom scene was generated by applying a Gaussian blurring and a zero-mean Gaussian noise, and finally by adding a fixed slow varying (ramp) background component across columns. FIGS. 2(a) and 2(b) represent the 2D scenes before and after adding noise, blurring, and background variation, respectively. The size of the scene was 185×232 with an in-plane resolution of 0.86×0.86 mm$^2$. FIGS. 2(d) and 2(f) were obtained by applying the anisotropic diffusion and scale-based diffusion methods, respectively.

In both cases, 10 iterations were used. A few more iterations than the recommended number were used for the anisotropic method to emphasize the diffusion across boundaries. On the other hand, when the process was run for fewer iterations, i.e., the recommended number of 3 iterations, the noise reduction was not significant, as can be seen from FIG. 2(c). It can be observed from FIGS. 2(d) and 2(f), that while the interior (homogeneous) regions were (visually) equally smooth in the two images, contrast at the boundaries is significantly improved in FIG. 2(f). A similar phenomenon, although to a lesser degree, can be observed between FIGS. 2(c) and (e).

It is unreasonable to expect that a filtering method will retrieve structures that are lost by any degradation in the imaging process. Therefore, some finer details seen in FIG. 2(a) were lost in FIG. 2(f). Given the degraded phantom of FIG. 2(b) as the starting scene, it appeared in the filtered scene in FIG. 2(f) that someone had carefully smoothed the scene while preserving the structures and boundaries as much as possible. However, any such action would require at least a rough knowledge of the object size at various points, which is exactly what is provided by scale.

Phantom Example 1.2.

The second phantom example was also a 2D phantom containing different geometric objects with varying shape, size and orientation. The entire phantom scene domain was divided into six square regions of equal size, three of which are at the top, and the other three are at the bottom. The initial phantom consisted of only two different intensity regions representing the objects (brighter) and the background (darker). This was generated by filling each of the six square regions with geometric objects of different size, shape and orientation.

From this initial binary scene, 25 phantom scenes were generated by blurring (using a 2D Gaussian kernel) the scene at 5 different degrees, and by adding a zero-mean Gaussian-correlated noise component at 5 levels. Each of the 25 scenes was further modified by adding a slow varying (ramp) background component which changed from 0 at the first column to 200 at the last column. Each of the resulting 25 scenes was filtered using the three filtering methods. One of the final phantom scenes, corresponding to a low level of blurring and a medium level of noise, is shown in FIG. 6(a). The size of the phantom scene was 800×600.

Due to the large size of the phantom, subtle details are not visible in the display of FIG. 6(a). The phantom scene, as well as the results using the three filtering methods, are shown in FIG. 7 over each of the six ROIs marked in FIG. 6(a). FIG. 7(a) depicts scenes within the six ROIs taken from the unfiltered phantom scene, while FIGS. 7(b)–7(d) depict the corresponding filtered scenes that resulted from anisotropic diffusion ((shown in FIG. 7(b)), from scale-based neighborhood averaging (shown in FIG. 7(c)), and from scale-based diffusion (shown in FIG. 7(d)).

Figure 6:
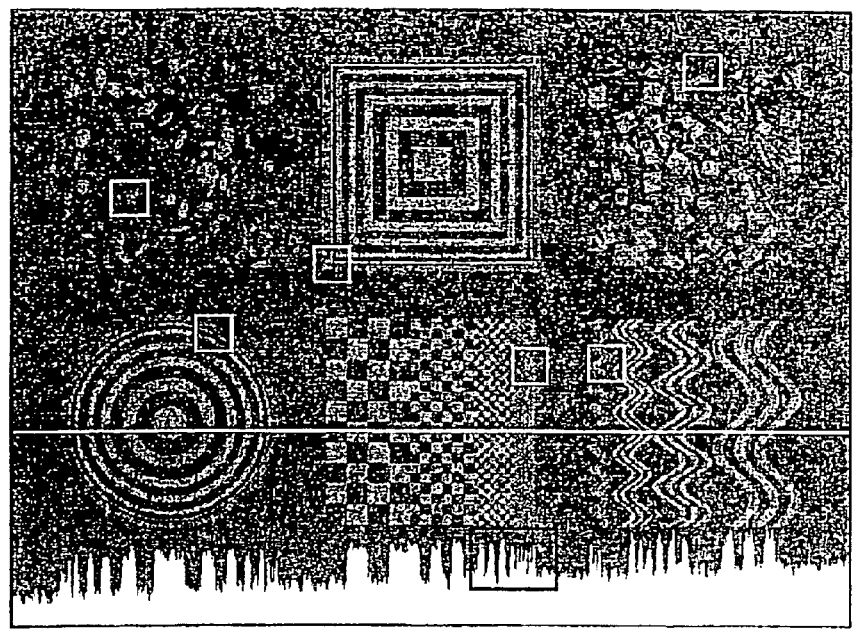
FIGS. 6(a)–6(f) depict comparisons among the three filtering methods using a 2D phantom scene containing different geometric shapes of different size and orientation.
Figure 6:
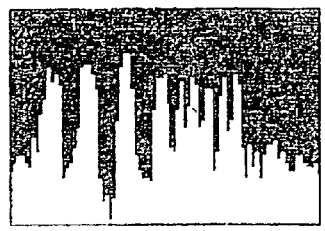
Figure 6:
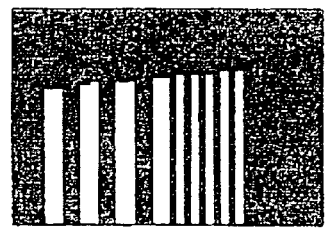
Figure 6:
Figure 6:
Figure 6:
Figure 7:
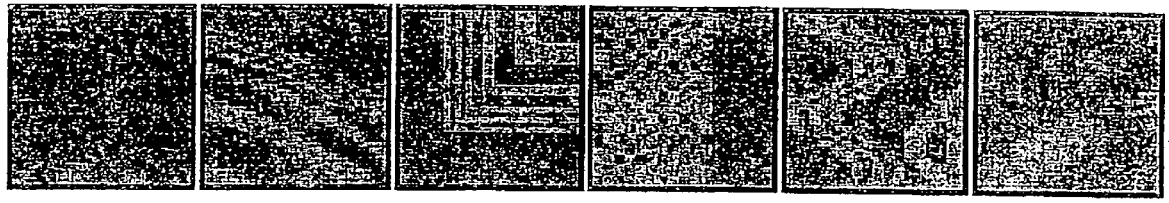
FIGS. 7(a)–7(d) depict comparisons among the three filtering methods using the 2D phantom scene of FIG. 6(a) for the six ROIs shown therein.
Figure 7:
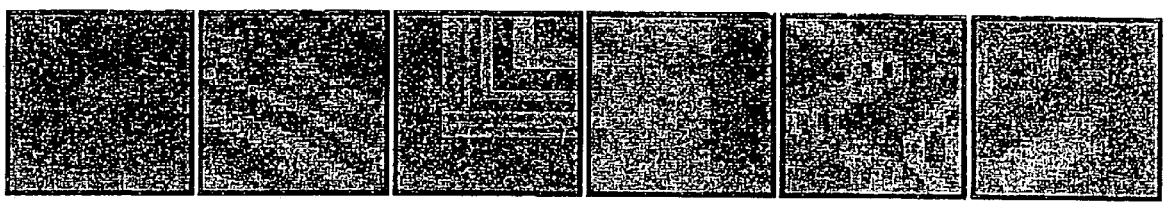
Figure 7:
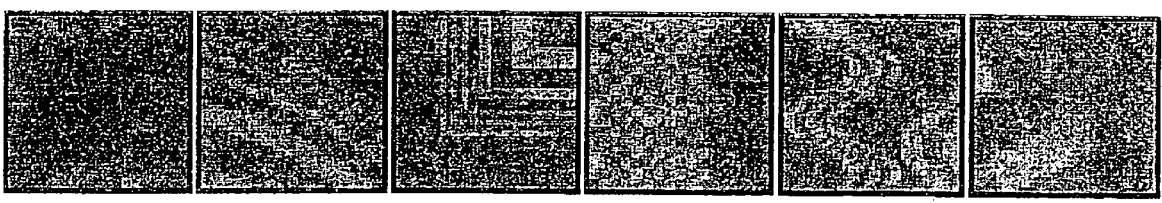
Figure 7:
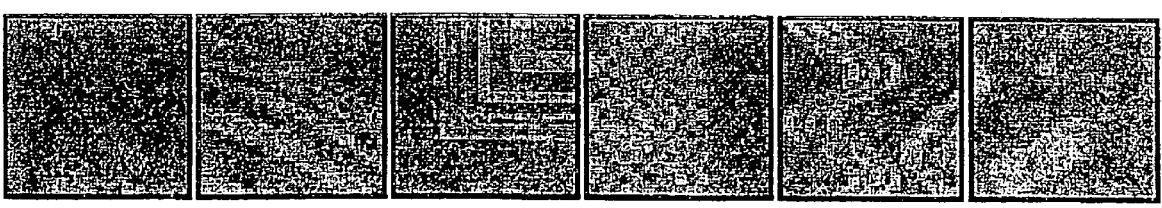

FIG. 6 also compares the three filtering methods via the intensity profile taken along a horizontal line, as shown in FIG. 6(a). FIG. 6(b) shows in magnification the profile over a small region indicated at the bottom of FIG. 6(a) (see rectangle outlined in black), and FIGS. 6(c)–(f) show four profiles corresponding to the same region in four different scenes—the initial phantom scene after adding only the ramp component (but not adding noise and blurring), and the filtered scenes obtained using anisotropic diffusion (shown in FIG. 6(d)), using scale-based neighborhood averaging (shown in FIG. 6(e)), and using scale-based diffusion (shown in FIG. 6(f)), respectively. In FIG. 6(d) (anisotropic filtering), the identities of the five (5) narrow, vertical columns, each representing a small square (see FIG. 7, 4th column), were lost; whereas by comparison, they were preserved by the scale-based methods (FIGS. 6(e) and 6(f)).

Meanwhile, filtering over each piecewise homogeneous region was also improved using scale-based diffusion, as compared with anisotropic diffusion. This was also visible in the background region shown in the ROI scenes. The first and the sixth columns in FIG. 7 were used to demonstrate the behavior of the three methods in homogeneous regions, while other columns demonstrate their behaviors in regions containing fine structures. Although all methods preserve large structures, the scale-based methods produced significantly improved results for finer structures.

Example 2

Quantitative Comparisons.

The quantitative comparison utilized the scenes depicted in FIGS. 6 and 7. Let $C_b = (C, f_b)$ denote the original binary phantom scene (before adding artifacts), and let $E = \{C_i | C_i = (C, f_i), 1 \leq i \leq 25\}$ denote the set of 25 phantom scenes generated from $C_b$, as described in Example 1, Phantom Example 1.2. Let let $E_{xi} = \{C_{xi} | C_{xi} = (C, 71_{xi}), 1 \leq i \leq 25\}$ denot the set of scenes produced by applying the filtering method $x \in \{ad, sa, sd\}$ to the scenes in E, where ad, sa, sd correspond to anisotropic diffusion, scale-based neighborhood averaging and scale-based diffusion, respectively. Over the scene domain C, 100 ROIs, $C^{Hi}$, $1 \leq i \leq 100$ were randomly selected, each of size 18×18, from homogeneous regions, such that all the pixels in a ROI had the same intensity (object or background) in the initial phantom scene $C_b$. Of the 100 ROIs, 60 were from background regions, and 40 were from object regions. Additionally, 50 ROIs, $C^{Si}$, $1 \leq i \leq 50$, were selected from regions containing boundaries. Each $C^{Si}$ was selected such that it contained pixels from both the object and background regions. Let $O_i$ and $B_i$ denote the set of pixels in $C^{Si}$ from the object and background regions, respectively.

For $x \in \{ad, sa, sd\}$ $1 \leq i \leq 25$, and $1 \leq j \leq 100$, "residual noise" $RN_{xi}^j$ was defined the standard deviation of pixel intensities $f_{xi}(c)$ over each homogeneous ROI $C^{Hj}$ in a filtered scene resulting from method x for the phantom scene at the level of blurring and noise given by the index i.

Tables 1, 2, 3 list in each cell, the mean and the standard deviation of $RN_{adi}^j$, $RN_{sai}^j$, and $RN_{sdi}^j$, respectively, at each degree of blurring and noise for the 100 ROIs. The degrees of blurring and noise increase along columns and rows, respectively, from the upper left corner.

TABLE 1

The mean (first entry) and standard deviation (second entry) of $RN_{adi}^j$ values are shown in each cell for different blurring and noise conditions. Noise increases along rows from left to right while blurring increases along columns from top to bottom.

|  | Noise 1 | Noise 2 | Noise 3 | Noise 4 | Noise 5 |
| --- | --- | --- | --- | --- | --- |
| Blur 1 | 6.036 | 8.438 | 10.948 | 13.457 | 16.009 |
|  | 0.966 | 1.278 | 1.632 | 1.984 | 2.341 |
| Blur 2 | 6.076 | 8.498 | 10.995 | 13.506 | 16.056 |
|  | 0.985 | 1.288 | 1.637 | 1.983 | 2.338 |
| Blur 3 | 6.035 | 8.503 | 11.086 | 13.683 | 16.606 |
|  | 0.973 | 1.298 | 1.658 | 2.015 | 2.395 |
| Blur 4 | 6.008 | 8.512 | 11.115 | 13.691 | 16.618 |
|  | 0.965 | 1.300 | 1.657 | 2.018 | 2.401 |
| Blur 5 | 5.987 | 8.502 | 11.111 | 13.694 | 16.625 |
|  | 0.963 | 1.299 | 1.658 | 2.021 | 2.401 |

TABLE 2

The mean (first entry) and standard deviation (second entry) of $RN_{sai}^j$ values are shown in each cell for different blurring and noise conditions. Noise increases along rows from left to right, while blurring increases along columns from top to bottom.

|  | Noise 1 | Noise 2 | Noise 3 | Noise 4 | Noise 5 |
| --- | --- | --- | --- | --- | --- |
| Blur 1 | 4.655 | 6.493 | 8.813 | 11.118 | 13.490 |
|  | 1.350 | 1.491 | 1.797 | 2.157 | 2.562 |
| Blur 2 | 4.683 | 6.661 | 8.938 | 11.244 | 13.602 |
|  | 1.339 | 1.611 | 1.893 | 2.226 | 2.598 |
| Blur 3 | 4.603 | 6.684 | 9.282 | 11.896 | 15.586 |
|  | 1.214 | 1.638 | 1.976 | 2.354 | 2.728 |
| Blur 4 | 4.580 | 6.806 | 9.415 | 11.913 | 15.604 |
|  | 1.170 | 1.543 | 1.932 | 2.371 | 2.743 |
| Blur 5 | 4.578 | 6.795 | 9.404 | 11.920 | 15.613 |
|  | 1.161 | 1.521 | 1.919 | 2.376 | 2.747 |

TABLE 3

The mean (first entry) and standard deviation (second entry) of $RN_{sdi}^j$ values are shown in each cell for different blurring and noise conditions. Noise increases along rows from left to right, while blurring increases along columns from top to bottom.

|  | Noise 1 | Noise 2 | Noise 3 | Noise 4 | Noise 5 |
| --- | --- | --- | --- | --- | --- |
| Blur 1 | 4.204 | 5.920 | 7.954 | 10.072 | 12.334 |
|  | 0.923 | 1.250 | 1.631 | 2.038 | 2.530 |
| Blur 2 | 4.223 | 5.966 | 7.979 | 10.114 | 12.401 |
|  | 0.924 | 1.269 | 1.646 | 2.051 | 2.529 |
| Blur 3 | 4.238 | 5.987 | 8.254 | 10.778 | 14.774 |
|  | 0.924 | 1.276 | 1.715 | 2.235 | 2.855 |
| Blur 4 | 4.239 | 6.100 | 8.417 | 10.785 | 14.785 |
|  | 0.924 | 1.298 | 1.747 | 2.241 | 2.854 |
| Blur 5 | 4.240 | 6.102 | 8.420 | 10.787 | 14.797 |
|  | 0.924 | 1.298 | 1.748 | 2.240 | 2.857 |

From Tables 1, 2, and 3, it can be seen that at every level of blurring and noise, mean residual noise is maximal for anisotropic diffusion, and it is minimal for scale-based diffusion. Moreover, at each level of blurring and noise, three paired t-tests (Rosner, *Fundamentals of Biostatistics*, New York, N.Y., Duxbury Press, 1995, each over 100 pairs ($RN_{xi}^j$ $RN_{yi}^j$), $x \neq y$, $x$, $y \in \{ad, sa, sd\}$, and $1 \leq j \leq 100$, of RN data produced by two different filtering methods, were conducted under the null hypothesis that there is no statistically significant difference between the two methods. The hypothesis was rejected at a very high level of confidence ($p<10^{-5}$) in all tests between a scale-based method and anisotropic diffusion. This confidence level was less than $0.3 \times 10^{-4}$ for the t-test between the two scale-based methods.

Obviously, a measure of residual noise alone is not sufficient to characterize the effectiveness of a filtering method. For this reason, a measure of "relative contrast" was defined, $RC_{xi}^j$ for $x \in \{ad, sa, sd\}$, $1 \leq i \leq 25$, $1 \leq j \leq 50$ as follows:

$$RC_{xi}^j = \frac{|M_{xi}^{Oj} - M_{xi}^{Bj}|}{\sqrt{\sigma_{xi}^{Oj} \sigma_{xi}^{Bj}}}, \quad \text{(Equation 18)}$$

wherein $M_{xi}^{Oj}$ and $\sigma_{xi}^{Oj}$ denote the mean and standard deviation, respectively, of pixel intensities $f_{xi}(c)$ over the object region $O_j$ and $M_{xi}^{Bj}$ and $\sigma_{xi}^{Bj}$ denote similar entities over the background region $B_j$. Notably, RC gives a measure of object-to-background contrast relative to residual noise in each region.

Tables 4, 5, and 6 list in each cell the mean and the standard deviation of $RC_{adi}^j$, $RC_{sai}^j$, and $RC_{sdi}^j$, respectively, at each degree of blurring and noise for the 50 ROIs. Notably, a higher value of RC signifies more accurate filtering.

TABLE 4

The mean (first entry) and standard deviation (second entry) of $RC_{adi}^j$ values are shown in each cell for different blurring and noise conditions. Noise increases along rows from left to right while blurring increases along columns from top to bottom.

|  | Noise 1 | Noise 2 | Noise 3 | Noise 4 | Noise 5 |
| --- | --- | --- | --- | --- | --- |
| Blur 1 | 7.983 | 6.448 | 5.185 | 4.048 | 3.240 |
|  | 3.400 | 2.076 | 1.317 | 0.772 | 0.478 |
| Blur 2 | 4.764 | 3.691 | 2.933 | 2.404 | 2.059 |
|  | 2.048 | 0.908 | 0.307 | 0.345 | 0.491 |
| Blur 3 | 2.286 | 2.002 | 1.784 | 1.674 | 1.609 |
|  | 0.348 | 0.561 | 0.651 | 0.682 | 0.641 |
| Blur 4 | 1.833 | 1.735 | 1.611 | 1.475 | 1.418 |
|  | 0.673 | 0.696 | 0.726 | 0.751 | 0.696 |
| Blur 5 | 1.638 | 1.561 | 1.468 | 1.365 | 1.307 |
|  | 0.755 | 0.749 | 0.753 | 0.758 | 0.700 |

TABLE 5

The mean (first entry) and standard deviation (second entry) of $RC_{sai}^j$ values are shown in each cell for different blurring and noise conditions. Noise increases along rows from left to right while blurring increases along columns from top to bottom.

|  | Noise 1 | Noise 2 | Noise 3 | Noise 4 | Noise 5 |
| --- | --- | --- | --- | --- | --- |
| Blur 1 | 7.755 | 6.340 | 5.372 | 4.627 | 4.010 |
|  | 2.645 | 1.455 | 0.860 | 0.556 | 0.412 |
| Blur 2 | 5.176 | 4.262 | 3.635 | 3.140 | 2.705 |
|  | 1.942 | 1.138 | 0.692 | 0.429 | 0.230 |
| Blur 3 | 3.311 | 2.679 | 2.184 | 2.002 | 1.860 |
|  | 0.919 | 0.289 | 0.244 | 0.344 | 0.369 |

TABLE 5-continued

The mean (first entry) and standard deviation (second entry) of $RC_{sai}^j$ values are shown in each cell for different blurring and noise conditions. Noise increases along rows from left to right while blurring increases along columns from top to bottom.

|  | Noise 1 | Noise 2 | Noise 3 | Noise 4 | Noise 5 |
| --- | --- | --- | --- | --- | --- |
| Blur 4 | 2.390 | 2.116 | 1.878 | 1.675 | 1.590 |
|  | 0.187 | 0.266 | 0.402 | 0.485 | 0.462 |
| Blur 5 | 1.881 | 1.780 | 1.638 | 1.501 | 1.426 |
|  | 0.396 | 0.434 | 0.495 | 0.528 | 0.502 |

TABLE 6

The mean (first entry) and standard deviation (second entry) of $RC_{sdi}^j$ values are shown in each cell for different blurring and noise conditions. Noise increases along rows from left to right while blurring increases along columns from top to bottom.

|  | Noise 1 | Noise 2 | Noise 3 | Noise 4 | Noise 5 |
| --- | --- | --- | --- | --- | --- |
| Blur 1 | 8.033 | 6.569 | 5.563 | 4.808 | 4.181 |
|  | 3.044 | 1.721 | 1.019 | 0.662 | 0.485 |
| Blur 2 | 5.341 | 4.386 | 3.738 | 3.250 | 2.847 |
|  | 2.238 | 1.328 | 0.809 | 0.503 | 0.294 |
| Blur 3 | 3.503 | 2.923 | 2.321 | 2.084 | 1.913 |
|  | 1.075 | 0.486 | 0.246 | 0.381 | 0.406 |
| Blur 4 | 2.690 | 2.226 | 1.905 | 1.673 | 1.583 |
|  | 0.423 | 0.237 | 0.445 | 0.585 | 0.530 |
|  | 1.902 | 1.766 | 1.612 | 1.481 | 1.412 |
| Blur 5 | 0.418 | 0.492 | 0.577 | 0.627 | 0.566 |

From Tables 4 and 6 it can be seen that, at every level of blurring and noise, the mean relative contrast for the scale-based filtering method is higher than that for anisotropic diffusion. At each level of blurring and noise, three paired t-tests each of 50 pairs of ($RC_{xi}^j$, $RC_{yi}^j$), $x \neq y$, $x$, $y \in \{ad, sa, sd\}$, and $1 \leq j \leq 50$, of RC data produced by two different filtering methods were conducted under the null hypothesis that there is no statistically significant difference between the two methods.

For the t-test between anisotropic diffusion and scale-based diffusion, the hypothesis was rejected at a very high level of confidence ($p<0.3 \times 10^{-4}$) at every level of blurring and noise, except for two (2) cases indicated by (Blur 1, Noise 1) and (Blur 1, Noise 2), in which two cases the results were not statistically significant. For the t-test between anisotropic diffusion and scale-based neighborhood averaging, the hypothesis was rejected at a very high level of confidence ($p<0.28 \times 10^{-3}$) at every level of blurring and noise, except for three (3) cases, which were at minimum blurring and the three lowest noise levels, and in which three cases the results were not statistically significant. For the t-test between the two scale-based methods, scale-based neighborhood averaging and scale-based diffusion, the hypothesis was rejected at a very high level of confidence ($p<0.6 \times 10^{-3}$) at every level of blurring and noise, except for six (6) cases, which were at maximum blurring and the four highest noise levels and at second maximum blurring and the two highest noise levels, and in which six cases the results were not statistically significant.

In conclusion, qualitative comparisons based on geometric phantoms generated under a range of conditions of blurring, noise and background variation, as well as patient MR images, indicate significant improvements and clear superiority using the scale-based filtering methods of the invention over the prior art anisotropic diffusion methods, for preserving boundary sharpness and fine details while suppressing noise. As between the two scale-based methods, results using scale-based diffusion have been found to be superior, except at extremely low blurring and noise where the differences were not statistically significant. Both scale-based methods embodying the invention use region-constancy based on local homogeneity to effect filtering. However, scale-based neighborhood averaging uses it in a hard fashion, while scale-based diffusion uses it in a fuzzy manner. Because of this difference in the basic strategy, results using scale-based diffusion were considered to be more visually pleasing than those using scale-based averaging. Since the same trend was observed in the quantitative experiments, scale-based diffusion was preferred over scale-based neighborhood averaging, although the latter is computationally the least expensive among the three methods.

Each and every patent, patent application and publication that is cited in the foregoing specification is herein incorporated by reference in its entirety.

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the spirit and scope of the invention. Such modifications, equivalent variations and additional embodiments are also intended to fall within the scope of the appended claims.

What is claimed is:

1. A method of scale-based, post-acquisition processing of an MRI-acquired image by variant anisotropic filtering to enhance structure and reduce noise, wherein the processing comprises adaptively modifying degree of filtering at any image location depending on local object size information or scale, effecting improved low signal-to-noise ratio, or improved low contrast-to-noise ratio, or both.

2. The method of claim 1, wherein filtering comprises a spatial-resolution adaptive scale-computation method.

3. The method of claim 1, comprising accurately using a restricted homogeneity parameter for filtering small scale regions of the image, and at the same time, using a generous filtering parameter for filtering large scale regions of the image.

4. The method of claim 3, wherein small scale regions comprise fine details and vicinities of boundaries of the image.

5. The method of claim 3, wherein large scale regions comprise interiors of homogeneous regions of the image.

6. The method of claim 3, wherein filtering comprises a scale-based neighborhood averaging method.

7. The method of claim 6, wherein filtering comprises a weighted average over a scale-dependent neighborhood.

8. The method of claim 3, wherein filtering comprises a scale-based diffusive filtering method.

9. The method of claim 8, wherein filtering comprises scale-dependent diffusion conductance.

10. The method of claim 1, wherein a scale-based, enhanced MRI-acquired image is achieved for a selected MRI protocol, and for a selected region of a patient's body, by the steps comprising:

a) imaging the region of the patient's body by the selected MR protocol to form an acquired image, and b) filtering the acquired image by a scale-based spatial resolution adaptive method using region-constancy based on local homogeneity to produce an enhanced image.

11. The method of claim 10, wherein the image is enhanced independently of variations within or between patients, within or between tissues being imaged, or within or between MR devices used to acquire the image.

12. The method according to claim 10, wherein the method is automated.

13. The method according to claim 10, which is built into an MR scanner, permitting production of enhanced real time images.

14. The enhanced MR image for imaging a region of the body of a patient according to claim 6.

15. The enhanced MR image for imaging a region of the body of a patient according to claim 8.

16. The enhanced MR image for imaging a region of the body of a patient according to claim 10.

17. A system for post-acquisition processing of an MRI-acquired image by a scale based filtering method, comprising:

means for acquiring the MRI-acquired image, and means for filtering the acquired image by a spatial-resolution adaptive scale-computation method according to claim 10.

18. The system according to claim 17, wherein the filtering method is a scale-based neighborhood averaging method or a scale-based diffusive filtering method.

19. A device for post-acquisition processing of an MRI-acquired image by a scale based filtering method, comprising:

a computer-readable signal-bearing medium;

means in the medium for acquiring the MRI-acquired image, and means for filtering the acquired image by a spatial-resolution adaptive scale-computation method according to claim 10.

20. The device according to claim 19, wherein the filtering method is a scale-based neighborhood averaging method or a scale-based diffusive filtering method.

* * * * *